United States Patent [19]

Lafon

[11] Patent Number: 4,705,795
[45] Date of Patent: Nov. 10, 1987

[54] (2,4,6-TRIMETHOXYPHENYL)-(3-PIPERIDINOPROPYL)-KETONE DERIVATIVES

[75] Inventor: Louis Lafon, Paris, France

[73] Assignee: Laboratoire L. Lafon, Maisons-Alfort, France

[21] Appl. No.: 829,565

[22] Filed: Feb. 14, 1986

Related U.S. Application Data

[63] Continuation of Ser. No. 545,174, Oct. 25, 1983, abandoned.

[30] Foreign Application Priority Data

Oct. 26, 1982 [FR] France ................... 82 17938

[51] Int. Cl.$^4$ ............... C07D 211/32; A61K 31/445
[52] U.S. Cl. .................... 514/317; 546/237; 514/929
[58] Field of Search ............... 546/237; 514/317, 929

[56] References Cited

U.S. PATENT DOCUMENTS 3,895,030 7/1975 Lafon .
4,031,101 6/1977 Fleming .
4,396,622 8/1983 Jozic .................... 546/232

FOREIGN PATENT DOCUMENTS 0063075 10/1982 European Pat. Off. .
1492256 7/1967 France .
1115992 6/1968 United Kingdom .
1218583 1/1971 United Kingdom .
2004883 4/1979 United Kingdom .

Primary Examiner—Norma S. Milestone
Attorney, Agent, or Firm—Schwartz, Jeffery, Schwaab, Mack, Blumenthal & Evans

[57] ABSTRACT

The present invention relates to new derivatives of (2,4,6-trimethoxyphenyl)-(3-piperidinopropyl)-ketone which are selected from the group consisting of:
(i) (2,4,6-trimethoxyphenyl)-[3-(alkylpiperidino)-propyl)]-ketones of general formula:

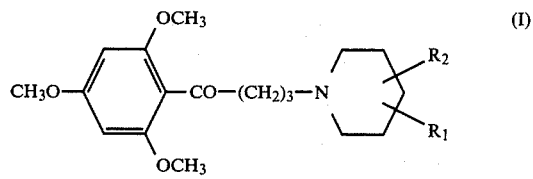

wherein
$R_1$ is $CH_3$ or $C_2H_5$ in 2- or 3-position of the piperidine ring, and
$R_2$ is H, $CH_3$ or $C_2H_5$; and
(ii) their addition salts. These new derivatives are useful in therapeutics.

6 Claims, No Drawings

(2,4,6-TRIMETHOXYPHENYL)-(3-PIPERIDINO-PROPYL)-KETONE DERIVATIVES

This application is a continuation of application Ser. No. 545,174, filed Oct. 25, 1983, abandoned.

BACKGROUND OF THE INVENTION

The present invention relates to (2,4,6-trimethoxyphenyl)-(3-piperidinopropyl)-ketone derivatives as novel industrial products. The invention also relates to the uses in therapeutics and the process of synthesis of these novel derivatives.

It is known that in the past a certain number of compounds of the phenyl-aminoalkyl-ketone type have been suggested where the amino residue is particularly a piperidino group. In particular there are known:

from French Patent No. 1 492 256, from the French Patent (BSM) No. 5636M and from the article of A. BOUCHERLE et al., Chimie Thérapeutique, 3 (No. 4), 256–259 (1968), the (2,4,6-trimethoxyphenyl)-[2-piperidino-ethyl]-ketone, (2,4,6-trimethoxyphenyl)- [2-(4-methylpiperidino)-ethyl]-ketone and [(2,4-dimethoxyphenyl)-[2-(2-methylpiperidino)-ethyl]]-ketone which have essentially anti-inflammatory, antalgic and antipyretic effects, on the one hand, and (2,4,6-trimethoxyphenyl)-[(2-methylpiperidino)-methyl]-ketone, which is a neuroleptic agent, on the other hand;

from British Patent No. 1,115,992, (2,4-dimethoxyphenyl)-(piperidinomethyl)-ketone and (2,4,6-trimethoxyphenyl)- [(4-methylpiperidino)-methyl]-ketone, which have essentially anti-spasmodic and tranquillising effects; and, from U.S. Pat. No. 3,895,030, (2,4,6-trimethoxyphenyl)-(3-piperidinopropyl)-ketone hydrochloride, which has essentially anti-spasmodic effects and which is useful in the treatment of renal colic, and (2,4,6-trimethoxyphenyl)-(3-pyrrolidinopropyl)-ketone hydrochloride (Code No. LL 1656), which is a reference peripheral vasodilator, which has formed the subject of publication by DEBRAY et al., Thérapie, 30, 259–266 (1975) and which is marketed in pharmacy under the name of "FONZYLANE" (International Common Name: BUFLOMEDIL HYDROCHLORIDE).

Lastly, it is known particularly from British Patent No. 2,004,883 and from European patent application No. 82,400,577.1, that there is no structure-activity relationship within the family of (alkoxy and hydroxyphenyl)-aminoalkyl-ketones, the pharmacological effects being modified or disappearing according to the nature of the substituents of the phenyl group, the nature of the amino group, and lastly, the nature of the alkyl group present between the CO group and the amino group.

It is known in particular from the aforesaid European patent application that (2,6-dimethoxy-4-hydroxyphenyl)-(3-piperidinopropyl)-ketone hydrochloride (Code No.: CRL 40,746) is a vasodilator agent whereas its isomer (2,4-dimethoxy-6-hydroxyphenyl)-(3-piperidinopropyl)ketone hydrochloride (Code No.: CRL 40,747) is devoid of pharmacological interest as a vasodilator substance by the intravenous route.

GENERAL DESCRIPTION OF THE INVENTION

It has just been discovered surprisingly that the novel derivatives of Formula I below and their addition salts (i) have vasodilator, hypotensive and bradycardiac properties beneficial in therapeutics, particularly in the treatment of disorders of the circulation, (ii) are distinguished from their previously-known homologues of the (2,4,6-trimethoxyphenyl)-(piperidinoalkyl)-ketone type by their vasodilator properties, the products according to the invention having a femoral vasodilator effect by the intraduodenal route in the anesthetised dog whereas the said homologues studied under the same conditions have no femoral vasodilator effect.

The novel derivatives of (2,4,6-trimethoxyphenyl)-(3-piperidinopropyl)-ketone according to the invention are characterised in that they are selected from the group consisting of:

(i) (2,4,6-trimethoxyphenyl)-[3-(alkylpiperidino)-propyl]-ketones corresponding to the general formula

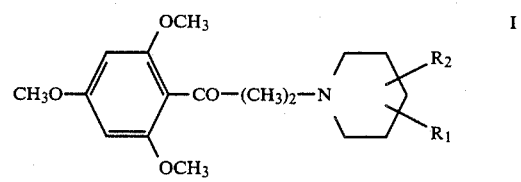

in which $R_1$ represents a $CH_3$ or a $C_2H_5$ group only in 2 or 3 position of the piperidino group, and $R_2$ represents H, $CH_3$ or $C_2H_5$; and (ii) their addition salts.

The preferred products according to the invention are the compound where $R_1 = 3—CH_3$ and $R_2 = H$, the compound where $R_1 = 3—CH_3$ and $R_2 = 5—CH_3$, and their salts.

By addition salts is meant here, on the one hand, the acid addition salts obtained by the reaction of a free base of Formula I with inorganic and organic acids and, on the other hand, ammonium salts. Among the acids usable to form salts of the bases of Formula I, may be mentioned particularly hydrochloric, hydrobromic, acetic, formic, propionic, oxalic, fumaric, maleic, succinic, benzoic, cinnamic, mandelic, citric, malic, tartaric, aspartic, glutamic, methanesulfonic, p-toluenesulfonic acids. Among the compounds enabling the ammonium salts to be obtained, may be mentioned particularly $ICH_3$ and $ClCH_3$. The acid addition salts are the preferred salts and, among the latter, the hydrochlorides are very interesting therapeutically.

The compounds according to the invention are useful in the treatment of cardiovascular disorders, particularly as vasodilator, hypotensive and bradycardiac agents. They are good medicaments for disorder associated with circulatory troubles and particularly the Raynaud syndrome.

According to the invention, there is recommended a therapeutic composition which contains, in association with a physiologically-acceptable excipient, at least one (2,4,6-trimethoxyphenyl)- [3-(alkylpiperidino)-propyl]-ketone of Formula I or one of its non-toxic addition salts, as active ingredient. In such a composition, the active ingredient is used at a pharmaceutically-effective amount.

The compounds of Formula I may be prepared by a method known in itself by the application of convventional reaction mechanisms. The method that is recommended consists in:

(a) reacting a piperidine of formula

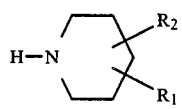

(where R₁ and R₂ as defined above) with 4-chlorobutyronitrile of the formula

Cl—(CH₂)₃—CN   III for at least 2h under reflux (preferably in the proportion of 2 moles of II for 1 mole of III), in the presence of an aromatic hydrocarbon such as benzene, toluene and their mixtures, to obtain the corresponding 4-(alkylpiperidino)-butyronitrile of the formula

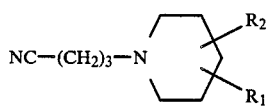

(where R₁ and R₂ are as defined above); and (b) reacting the 4-(alkylpiperidino)-butyronitrile compound so obtained with 1,3,5-trimethoxybenzene in the presence of a gaseous flow of HCl at a temperature comprised between −5° C. and +5° C. for at least 2h in an anhydrous solvent (particularly selected from the group consisting of benzene, toluene, chlorobenzene and their mixtures), then subjecting the ketimine derivative so formed to a hydrolysis reaction for at least 0.5h at the reflux temperature of the reaction medium.

Advantageously, the reaction of stage b) between the 4-(alkylpiperidino)-butyronitrile and the 1,3,5-trimethoxybenzene will be employed under stoichiometric conditions in chlorobenzene, the ketimine derivative being formed then being hydrolysed without having been isolated from the reaction medium.

There are grouped in Tables I, II and III below a certain number
of products according to the invention (Example 1 to Example 5) which are in no way limiting but given purely by way of illustration,
comparison products (CP-1 to CP-12) and
intermediate products (A-1 to A-5) entering into the synthesis of the products according to the invention.

TABLE I

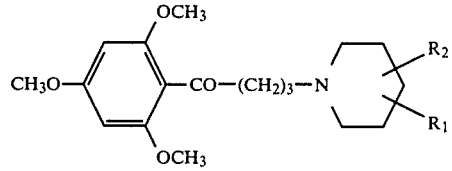

| Product | Code No | R₁ | R₂ | Recrystal- lisation Solvent | Melting Point |
|---|---|---|---|---|---|
| Example 1 (a) | CRL 41 008 | 2-CH₃ | H | (b) | 163° C. |
| Example 2 (a) | CRL 41 034 | 3-CH₃ | H | (c) | 110° C. |
| Example 3 (a) | CRL 41 035 | 2-C₂H₅ | H | (d) | 130° C. |
| Example 4 (a) | CRL 41 043 | 3-CH₃ | 5-CH₃ | (d) | 167° C. |
| Example 5 (a) | CRL 41 044 | 2-CH₃ | 6-CH₃ | (d) | 148° C. |

TABLE I-continued

| Product | Code No | R₁ | R₂ | Recrystal- lisation Solvent | Melting Point |
|---|---|---|---|---|---|
| 5 (a) CP-1 (a)(f) | — | H | H | (e) | 210–215 |
| CP-2 (a)(g) | CRL 41 007 | 4-CH₃ | H | (b) | 160° C. |

Notes
(a) Hydrochloride
(b) isopropanol
(c) isopropanol-ethyl acetate (1:5) v/v
(d) isopropanol-ethyl acetate (1:3) v/v
(e) ethanol water (50:1) v/v
(f) described in Example 14 of U.S. Pat. No. 3,895,030
(g) suggested by U.S. Pat. No. 3,895,030

TABLE II

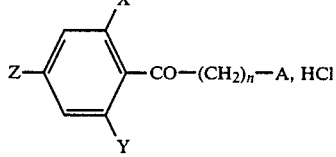

| Product | Code No | X | Y | Z | n | A |
|---|---|---|---|---|---|---|
| CP-3 (a) | — | — | OCH₃ | OCH₃ | OCH₃ | 2 | piperidino |
| CP-4 (a) | — | — | OCH₃ | OCH₃ | OCH₃ | 2 | 4-methyl-piperidino |
| CP-5 (b) | — | — | OCH₃ | H | OCH₃ | 1 | piperidino |
| CP-6 (b) | — | — | OCH₃ | OCH₃ | OCH₃ | 1 | 4-methyl-piperidino |
| CP-7 (c) | — | — | OH | OH | OH | 3 | piperidino |
| CP-8 (d) | CRL 40 747 | — | OCH₃ | OCH₃ | OH | 3 | piperidino |
| CP-9 (e) | — | — | OCH₃ | OCH₃ | OCH₃ | 1 | 2-methyl-piperidino |
| CP-10 (e) | — | — | OCH₃ | H | OCH₃ | 2 | 2-methyl-piperidino |
| CP-11 (d) | CRL 40 746 | — | OCH₃ | OH | OCH₃ | 3 | piperidino |
| CP-12 (c) | IL 1656 | OCH₃ | OCH₃ | OCH₃ | OCH₃ | 3 | pyrrolidino |

Notes
(a) described in French patents no 1 492 256 and no 5 636M
(b) described in British patent no 1 115 992
(c) described in U.S. Pat. No. 3,895,030
(d) described in European patent application no 82 400 577.1
(e) described by Boucherle et al. Chimie Therapeutique 3 (no 4), pages 256–259 (1968)

TABLE III

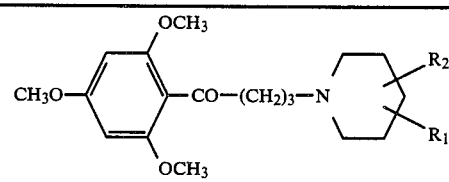

| Product | Synthesis Intermediate for | R₁ | R₂ | b.p. 5-mmHg |
|---|---|---|---|---|
| A-1 | example 1 | 2-CH₃ | H | 102° C. |
| A-2 | example 2 | 3-CH₃ | H | 100° C. |
| A-3 | example 3 | 2-C₂H₅ | H | 115–116° C. |
| A-4 | example 4 | 3-CH₃ | 5-CH₃ | 109–110° C. |

TABLE III-continued

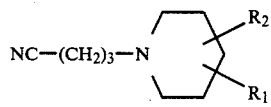

| Product | Synthesis Intermediate for | R1 | R2 | b.p. 5-mmHg |
|---|---|---|---|---|
| A-5 | example 5 | 2-CH3 | 6-CH3 | 114–116° C. |

Note
5–6 mmHg correspond approximately to 660–800 pascals

Other advantages and features of the invention will be better understood on reading the following description of examples of the preparation which are in no way limiting, on the one hand, and of the summary of tests which have been undertaken particularly on the pharmacological aspect, on the other hand.

DESCRIPTION OF PREFERRED EMBODIMENTS

PREPARATION I

Preparation of 2,4,6-trimethoxyphenyl [3-(3-methylpiperidino) -propyl]-ketone

Example 2; Code N°.:CRL 41 034

(a) 4-(3-methylpiperidion)-butyronitrile

In a solution under reflux of 58.6 ml (0.50 mole) of 3-methylpiperidine in 65 ml of benzene, were run in 25 minutes 27.2 g (0.25 mole) of 4-chlorobutyronitrile Reflux was continued for 2h, the precipitate was removed by filtration and the filtrate brought to dryness under reduced pressure. The residue from the evaporation was purified by distillation under reduced pressure to give 29.2 g (yields=70.3%) of 4-(3-methylpiperidino)-butyronitrile which was in the form of a colourless oil. Boiling point 5–6 mmHg =100° C.

(b) CRL 41 034

In a solution kept at about 0° C. and comprising 20.2 g (0.12 mole) of 1,3,5-trimethoxybenzene and 20g (0.12 mole) of 4-(3-methylpiperidino)-butyronitrile in 100ml of anhydrous chlorobenzene, was passed for 2.5h a flow of dry HCl gas, and it was left to stand 1.5h at a temperature of about 0° C. The reaction medium was extracted with water, and the aqueous phase brought to reflux for 1h. It was washed with diethyl ether, made alkaline with NH4OH and the precipitate formed extracted by means of diethyl ether. The resulting organic phase which contains the free base, namely (2,4,6-trimethoxyphenyl) -[3-(3-methylpiperidino)-propyl]-ketone, is treated with hydrochloric ethanol, the precipitate obtained is purified by recrystallisation from the isopropanol-ethylacetate (1:5) v/v mixture to give 27 g [yield of stage (b): 60.5%; overall yield 42.5%]of CRL 41 034 which is in the form of a water soluble white powder. MP inst (Köfler) =100° C.

PREPARATION II

Preparation of (2,4,6-trimethoxyphenyl)-[3-(3,5-dimethylpiperidino)-propyl]-ketone hydrochloride Example 4 code n°.: CRL 41 043

(a) 4-(3,5-dimethylpiperidino)-butyronitrile

Into a solution under reflux of 50 g (0.424 mole) of 3,5 dimethylpiperidine at 96% in 60 ml benzene are run in25 minutes 22 g (0.212 mole) of 4-chlorobutyronitrile and the reflux is continued for 2h.

The precipitate is removed by filtration and the filtrate is taken to dryness by evaporation under vacuum. The evaporation residue is purified by distillation under reduced pressure to give 26 g (yield=68.13%) of 4-(3,5-dimethylpiperidine)-butyronitrile in the form of a colourless oil b.p. 5–6 mmHg=109°–110° C.

(b) CRL 41 043

Into a solution kept towards 0° C. of 20.2 g (0.12 mole) of 1,3,5-trimethoxybenzene and of 21.6 g (0.12 mole) of 4-(3,5-dimethylpiperidine)-butyronitrile in 100 ml anhydrous chlorobenzene, is passed for 2h a dry current of HCl gas and it was left over ice for 2h. The reaction medium is extracted with water, then the aqueous phase is taken under reflux for 1.5h. It is made alkaline with caustic soda and the precipitate is extracted with diethyl ether to obtain 34.1 g of (2,4,6-trimethoxyphenyl-[3-(3,5-dimethylpiperidine)-propyl]-ketone which is in the form of a light orange oil. The free base is treated in diethyl ether with hydrochloric ethanol.

After purification of the precipitate by means of two successive recrystalisations from the isopropanol-ethyl acetate mixture (1:3) v/v are obtained 16 g [yield of stage(b): 34.6%; overall yield 23.6%]of CRL 41 043 which is in the form of a water soluble white powder. MP inst (Köfler)=167° C.

PREPARATION III

Production of (2,4,6-trimethoxyphenyl)-[3-(2,6-dimethylpiperidino)-propyl]-ketone hydrochloride Example 5; code n°.: CRL 41 044

(a) 4-(2,6-dimethylpiperidino)-butyronitrile

A solution of 50 g (0.438 mole) of 2,6-dimethylpiperidine and of 22.6 g (0.219 mole) of 4-chlorobutyronitrile are heated under reflux for 4 h in 50 ml of benzene. The precipitate is removed by filtration and the filtrate brought to dryness. The evaporation residue so obtained is purified by distillation under reduced pressure to give 11 g (yield=27.9%) of 4-(2,6-dimethylpiperidine)-butyronitrile in the form of a colourless oil. B.p. 5–6 mmHg=114°–116° C.

(b) CRL 41 044

Into a solution kept at 0° C. of 18.2 g (0.108 mole) of 1,3,5-trimethoxybenzene and of 19.5 g (0.108 mole) of 4-(2,6-dimethylpiperidine)-butyronitrile in 100 ml of anhydrous chlorobenzene, is passed for 2.5h a flow of dry HCl gas and the reaction medium was left overnight over ice. The reaction medium is extracted with water and the aqueous phase taken to reflux for 1.5h. It is made alkaline with sodium hydroxide and the precipitate extracted with diethyl ether to obtain 34.2 g of (2,4,6-trimethoxyphenyl)-[3-(3,5-dimethylpiperidine)-oily propyl]-ketone in the form of an orange oil. The oil free base is treated in diethyl ether with hydrochloric ethanol. After purification of the precipitate by recrystallisation from the mixture isopropanol-ethyl acetate (1:3) v/v are obtained 9.5 g [yield of stage b:22.8%; overall yield: 6.4%]of CRL 41 044 which is in the form of a white powder having a water solubility of the order of 100g/1.

Mp inst (Köfler)=148° C.

Below are summarised the tests which have been undertaken with the products according to the invention.

A—COMPARATIVE TESTS

The products according to the invention are compared with their structural analogues (CP-1 to CP-11) and a reference peripheral vasodilator which is LL 1656 (CP-12) mentioned previously.

The peripheral vasodilator properties have been studied in the anesthetized male dog with nembutal (6 animals per dose and per product). The products to be compared were administered in solution in physiological serum in a volume of 6 ml/animal intravenously (perfusion of 1 ml/min.). With respect to the controls (the same animals only receiving phsiological serum), three parameters were measured: the average blood pressure (expressed in mmHg; 1 mmHg corresponds to $1.333224 \times 10^2$ Pa), the heart rate (expressed beats/minute) and the femoral artery flow rate (expressed in ml/min). The variations of these parameters expressed in percentages with respect to the controls, are given in Table IV below.

The results of Table IV show the interest of the product according to the invention Ex 1 to Ex 5 with respect to their piperidino homologues CP-1 to CP-11, on the one hand, and with respect to the product of the pyrrolidino type, CP-12, on the other hand.

TABLE IV

Variation in the parameters after intravenous administration in the anesthetized dog

| Product | Code No. | Dose (mg/kg) | Blood Pressure | Femoral Artery Flow Rate | Heart rate |
|---|---|---|---|---|---|
| | | | | Variations in % | |
| Ex. 1 | CRL 41 008 | 1.5 | 0 | +8 | −10 |
| Ex. 2 | CRL 41 034 | 1.5 | −2 | +5 | +14 |
| Ex. 3 | CRL 41 035 | 1.5 | +5 | +47 | +2 |
| Ex. 4 | CRL 41 043 | 1.5 | +5 | +53 | +5 |
| Ex. 5 | CRL 41 044 | 1.5 | +3 | +27 | −1 |
| CP-1 | — | 1.5 | +1 | +10 | −2 |
| CP-2 | CRL 41 007 | 1.5 | +1 | +8 | −1 |
| CP-3 | — | 1.5 | +3 | +8 | −1 |
| CP-4 | — | 1.5 | −2 | +3 | −2 |
| CP-5 | — | 1.5 | −1 | −5 | +1 |
| CP-6 | — | 1.5 | +1 | +7 | +3 |
| CP-7 | — | 1.5 | +1 | +10 | −2 |
| CP-8 | CRL 40 747 | 1.5 | +2 | +20 | +5 |
| CP-9 | — | 1.5 | −1 | −4 | +1 |
| CP-10 | — | 1.5 | −2 | +2 | −1 |
| CP-11 | CRL 40 746 | 1.5 | +2 | +34 | +2 |
| CP-12 | LL 1656 | 1.5 | 0 | +33 | +5 |
| Ex. 1 | CRL 41 008 | 2 | 0 | +22 | −5 |
| Ex. 2 | CRL 41 034 | 2 | −6 | +24 | +19 |
| Ex. 3 | CRL 41 035 | 2.5 | +6 | +45 | 0 |
| Ex. 4 | CRL 41 043 | 2 | −2 | +87 | −14 |
| Ex. 5 | CRL 41 044 | 2.5 | +5 | +21 | 0 |
| CP-1 | — | 3 | +1 | +18 | +3 |
| CP-2 | CRL 41 007 | 3 | +2 | +10 | +2 |
| CP-3 | — | 3 | −2 | +8 | −6 |
| CP-4 | — | 3 | −5 | +2 | +1 |
| CP-5 | — | 3 | −8 | −8 | +3 |
| CP-6 | — | 3 | −1 | +5 | −2 |
| CP-7 | — | 3 | +1 | +18 | +3 |
| CP-8 | CRL 40 747 | 3 | −12 | +22 | −2 |
| CP-9 | — | 3 | −1 | +4 | −1 |
| CP-10 | — | 3 | −3 | +3 | +2 |
| CP-11 | CRL 40 746 | 3 | +5 | +35 | +3 |
| CP-12 | LL 1656 | 3 | −2 | +36 | +6 |
| Ex. 1 | CRL 41 008 | 5 | −4 | +40 | −5 |
| Ex. 2 | CRL 41 034 | 5 | −25 | +65 | −2 |
| Ex. 3 | CRL 41 035 | 5 | −2 | +79 | −8 |
| Ex. 4 | CRL 41 043 | 4 | −15 | +40 | −26 |
| Ex. 5 | CRL 41 044 | 5 | +1 | +46 | −7 |
| CP-1 | — | 6 | +2 | +34 | +3 |
| CP-2 | CRL 41 007 | 6 | +3 | +18 | +2 |
| CP-3 | — | 6 | +5 | +3 | −1 |
| CP-4 | — | 6 | +1 | +2 | −1 |
| CP-5 | — | 6 | −2 | −3 | +2 |
| CP-6 | — | 6 | −8 | +2 | +1 |
| CP-7 | — | 6 | +2 | +34 | +3 |
| CP-8 | CRL 40 747 | 6 | −18 | +22 | −15 |
| CP-9 | — | 6 | −3 | −2 | +2 |
| CP-10 | — | 6 | +3 | +2 | −2 |
| CP-11 | CRL 40 746 | 6 | +5 | +41 | +3 |
| CP-12 | LL 1656 | 6 | −2 | +39 | 0 |

The intraduodenal vasodilator properties have been studied in the anesthetized dog with nembutal. By the operational procedure given above, the products to be tested were administered in solution in physiological serum in a volume of 10 ml/animal intraduodenally. By this mode of administration, there was observed a distinct increase in the femoral artery blood flow from 2.5 mg/kg for the product of example 4 and from 5 mg/kg for the products of examples 1-3 and 5, whereas doses of 20 mg/kg are necessary for CRL 40 746 (CP-11) and LL 1656 (CP-12) to have the same increase. It is also observed, after intraduodenal administration, that a hypotensive effect and a bradycardiac effect are manifested from the dose of 5 mg/kg for the product of example 4 and from the dose of 10 mg/kg for the products of examples 1-3 and 5, whereas the dose of 20 mg/kg is necessary to obtain the same effects with CP-11 and CP-12.

B—TESTS RELATING TO CRL 41 034 (example 2)

I—FEMORAL VASODILATOR ACTION BY THE INTRAVENOUS ROUTE

Two dogs (average weight: 10.4 kg) anesthetized with pentobarbital received CRL 41034 intravenously by perfusion in 6 minutes, successive doses of 1,2 and 4 mg/kg separated from one an other by about one hour. One received an additional dose of 8 mg/kg. For comparison, these animals also received a perfusion of 6 mg/kg I.V. of LL 1656.

With CRL 41 034 a tachycardia was observed from the dose of 1 mg/kg. A distict increase in the femoral flow appeared at 4 mg/kg; it lasted more than 15 minutes and disappeared at 60 minutes; it was accompanied by hypotension. The effect of 2 mg/kg of CRL 41 034 on the femoral blood flow was on the average comparable with the effect of 6 mg/kg I.V. of LL 1656.

In one dog, the LL 1656 was perfused at 6 mg/kg at the start of the test and this dose had the same effect, on the femoral blood flow, as 2 mg/kg of CRL 41 034 (+60% at 6 minutes, +40% at 15 minutes, and disappearance of the effect at 30 minutes).

In the other dog, the LL 1656 is perfused at 6 mg/kg at the end of the test after the dog has received in total 15 mg/kg I.V. of CRL 41 034 and at a moment when the femoral blood flow is again increased by CRL 41 043. It is observed that the CRL 41 034 increases and prolongs the effect of LL 1656 on the femoral blood flow since at 30 minutes, the increase in the femoral flow rate (with respect to its value before any treatement) is again 150%.

II—VASODILATOR ACTION INTRADUODENALLY

Three dogs (average weight: 13.5 kg) anesthetized with nembutal received CRL 41 034 intraduodenally, at the successive doses of 0.1, 0.5, 1,2,5 and 10 mg/kg.

The blood pressure, the heart rate, the femoral artery flow rate, the vertebral artery flow rate, and the rectal temperature were measured, and the colour of the skin and the colour of the bile collected by catheterisation from the bile duct after ligature of the cystic duct were noted.

A considerable increase in the femoral blood flow was observed from the dose of 5 mg/kg. A hypotensive effect and a bradycardia appeared at 10 mg/kg. No increase in the vertebral flow rate was noted. The rectal and cutaneous temperatures did not vary; no modification of the skin and of the bile was observed.

C—TESTS RELATING TO CRL 41 035 (example 3)

Two dogs (average weight: 14.5 kg) anesthetized with nembutal received CRL 41 035 intraduodenally, at successive doses of 0.5 mg/kg, 1 mg/kg, 2.5 mg/kg, 5 mg/kg, and 10 mg/kg; one dog received an additional dose of 10 mg/kg I.V.

The blood pressure, the femoral artery blood flow, the vertebral artery blood flow and the rectal temperatures were measured. The colour of the skin and the colour of the bile collected by the catheterisation of the bile duct after ligature of the cystic duct was observed.

The CRL 41 035 studied in two anesthetized dogs showed itself to be hypotensive at the dose of 10 mg/kg I.D. by the drop of the systolic blood pressure and bradycardia. An increase in the femoral blood flow at 5 mg/kg was noted which remained present at 10 mg/kg in spite of the considerable hypotension; through this fact, the femoral resistance diminishes. No vertebral vasodilation was observed. The additional dose of 10 mg/kg injected in the dog confirmed the hypotension —41% (139 to 82 mmHg) at 30 minutes, the bradycardia —35% (155 to 100 beats/minutes) and the moderate increase but still present of the femoral blood flow +12% (43 to 48 ml/min).

The rectal and cutaneous temperatures did not vary. The colour of the skin and the bile was not modified.

The effects of isoprenalin tested after the cumulated dose of 19 mg/kg were slightly diminished on the heart rate and increased on the diastolic blood pressure At 3 mcg/kg of isoprenalin, the diastolic blood pressure passed to 32 mmHg instead of 56 mmHg and the heart rate passed to 210 beats/minute instead of 245 beats/minute as a control value.

The hypertension with noradrenalin was considerably reduced on the sistolic blood pressure. At 2 mcg/kg of noradrenalin, the systolic blood pressure passed to 196 mmHg instead 256 mmHg.

D—TESTS RELATING TO CRL 41 043 (example 4)

I—FEMORAL VASODILATOR ACTION INTRAVENOUSLY.

Four dogs (average weight 11.7 kg) anesthetized with nembutal received CRL 41 043 intravenously, in perfusion of 6 min, at successive doses of 1 and 2 mg/kg; three of these dogs then received 6 mg/kg of LL 1656, then 4 mg/kg of CRL 41 043.

CRL 41 043, at 1 mg/kg, increased the femoral blood flow for the duration of the perfusion without distinctly modifying the other parameters.

The dose of 2 mg/kg had a more intense and more lasting effect on the femoral blood flow which increased for 15 mins. The additional dose of 4 mg/kg increased the femoral blood flow less and resulted in hypotension and bradycardia. LL 1656, 6 mg/kg I.V., had the same effect on the femoral blood flow as 2 mg/kg I.V. of CRL 41 043.

I—FEMORAL VASODILATOR EFFECT INTRADUODENALLY

Three dogs (average weight 18.3 kg) anesthetized with nebutal received CRL 41 043 intraduodenally, at the successive doses of 0.1, mg/kg, 0.5 mg/kg, 1 mg/kg, 2.5 mg/kg, and 5 mg/kg.

It was observed that CRL 41 043 increased the femoral blood flow from the dose of 2.5 mg/kg. Hypotension and bradycardia appeared from the dose of 5 mg/kg, the increase in the femoral flow rate was restored when the hypotension disappeared. No increase in the vertebral flow rate was observed. The rectal and skin temperatures diminished moderately. At the dose of 5 mg/kg it was observed that the increase in the femoral flow rate was maximal 30 min after administration, the femoral vasodilator effect disappearing 1h after administration.

E—CLINICAL TESTS

In man, CRL 41 043 (Example 2) in the form of tablets or capsules each containing 0.75 g of active principle proved to be, at the rate of 2 to 3 tablets or capsules daily, a good medicament for circulatory disorders and particularly the Raynaud syndrome.

In man, CRL 41 043 (Example 4) in the form of tablets each containing 0.5 g of active principle was found, at the dosage rate of 2 to 3 tablets per day, to be a good peripheral vasodilator medicament.

What is claimed is:

1. A (2,4,6-trimethoxyphenyl)-(3-piperidinopropyl)-ketone compound selected from the group consisting of (2,4,6-trimethoxyphenyl)-[3-(2-methylpiperidino)-propyl]ketone, (2,4,6-trimethoxyphenyl)-[3-(3-methylpiperidino)propyl]-ketone, (2,4,6-trimethoxyphenyl)-[3-(2-ethylpiperidino)-propyl]-ketone, (2,4,6-trimethoxyphenyl)-[3-(3,5-dimethylpiperidino)-propyl]-ketone, (2,4,6-trimethoxyphenyl)-[3-(2,6-dimethylpiperidino)-propyl]-ketone, and non-toxic acid addition salts thereof.

2. A pharmaceutical composition comprising a physiologically acceptable excipient and an effect blood circulation enhancing amount of a compound selected from the group consisting of (2,4,6-trimethoxyphenyl)-[3-(2-methylpiperidino)-propyl]-ketone, (2,4,6-trimethoxyphenyl)-[3-(3-methylpiperidino)-propyl]-ketone, (2,4,6-trimethoxyphenyl)[3-(2-ethylpiperidino)-propyl]-ketone, (2,4,6-trimethoxyphenyl)-[3-(3,5-dimethylpiperidino)-propyl]-ketone, (2,4,6-trimethoxyphenyl)-[3-(2,6-dimethylpiperidino)-propyl]ketone, and non-toxic acid addition salts thereof.

3. A method of treating a circulation disorder in a mammal comprising administering to said mammal an effective blood circulation enhancing amount of a compound selected from the group consisting of (2,4,6-trimethoxyphenyl)-[3-(2-methyl-piperidino)-propyl]-ketone, (2,4,6-trimethoxyphenyl)-[3-(3-methylpiperidino)-propyl]-ketone, (2,4,6-trimethoxyphenyl)-

[3-(2-ethylpiperidino)-propyl]-ketone, (2,4,6-trimethoxyphenyl)-[3-(3,5-dimethylpiperidino)-propyl]-ketone, (2,4,6-trimethoxyphenyl)-[3-(2,6-dimethylpiperidino)-propyl]-ketone, and non-toxic acid addition salts thereof.

4. (2,4,6-trimethoxyphenyl)-[3-(3-methylpiperidino)-propyl]-ketone or a non-toxic acid addition salt thereof.

5. A pharmaceutical composition comprising a physiologically acceptable excipient and an effective blood circulation enhancing amount of (2,4,6-trimethoxyphenyl)-[3-(3-methylpiperidino)-propyl]-ketone or a non-toxic acid addition salt thereof.

6. A method of treating a circulation disorder in a mammal comprising administering to said mammal an effective blood circulation enhancing amount of (2,4,6-trimethoxyphenyl)-[3-(3-methylpiperidino)-propyl]-ketone or a non-toxic acid addition salt thereof.

* * * * *